(12) United States Patent
Kaiami et al.

(10) Patent No.: US 9,710,942 B2
(45) Date of Patent: Jul. 18, 2017

(54) BIOLOGICAL INFORMATION DISPLAYING APPARATUS AND BIOLOGICAL INFORMATION DISPLAYING METHOD

(71) Applicant: NIHON KOHDEN CORPORATION, Tokyo (JP)

(72) Inventors: Takashi Kaiami, Tokyo (JP); Tsuneo Takayanagi, Tokyo (JP); Masami Tanishima, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 107 days.

(21) Appl. No.: 14/717,056

(22) Filed: May 20, 2015

(65) Prior Publication Data

US 2016/0342827 A1    Nov. 24, 2016

(51) Int. Cl.
*G06K 9/00* (2006.01)
*G06T 11/20* (2006.01)
*A61B 5/02* (2006.01)

(52) U.S. Cl.
CPC .............. *G06T 11/206* (2013.01); *A61B 5/02* (2013.01); *G06K 9/0051* (2013.01)

(58) Field of Classification Search
CPC ............. G06F 19/3406; G06F 19/3418; G06F 19/3481; G06F 19/3443; G06F 19/345; A61N 1/36592; A61N 1/37; G01D 7/005; G01D 7/02
See application file for complete search history.

(56) References Cited

U.S. PATENT DOCUMENTS

| 2004/0260192 | A1* | 12/2004 | Yamamoto | A61B 5/044 600/523 |
| 2005/0115561 | A1* | 6/2005 | Stahmann | A61B 5/0031 128/200.24 |
| 2011/0021936 | A1* | 1/2011 | Luo | A61B 5/044 600/523 |
| 2012/0203124 | A1* | 8/2012 | Lim | A61B 5/0404 600/523 |
| 2013/0231947 | A1* | 9/2013 | Shusterman | G06F 19/3443 705/2 |

FOREIGN PATENT DOCUMENTS

JP          2010-57616 A       3/2010

* cited by examiner

*Primary Examiner* — Ali Bayat
(74) *Attorney, Agent, or Firm* — Pearne & Gordon LLP

(57) ABSTRACT

A biological information displaying apparatus includes: a measuring section which is configured to measure a biological information waveform containing a specific measurement value; a calculating section which is configured to calculate the specific measurement value based on the biological information waveform that is measured by the measuring section in a designated unit time; a determining section which is configured to determine a level of a reliability of the specific measurement value that is calculated by the calculating section, based on the biological information waveform that is measured by the measuring section in the unit time; and a displaying section which is configured to display a trend graph of the specific measurement values while the specific measurement values are distinct according to the level of the reliability that is determined by the determining section.

33 Claims, 6 Drawing Sheets

REPRESENTATIVE VALUE
MOVING AVERAGE

BIOLOGICAL INFORMATION DISPLAYING APPARATUS AND BIOLOGICAL INFORMATION DISPLAYING METHOD

BACKGROUND

The present invention relates to a biological information displaying apparatus, and a biological information displaying method.

A doctor or the like checks temporal transitions of, for example, measurement values of biological information which is periodically generated from the living body of a patient, to know the condition of the patient and detect abnormality.

However, measured biological information contains noises caused by a body motion of the patient, disturbances, and the like. In the case where a measured value is varied, it is difficult to determine whether the variation of the measurement value is caused by a change of the living body of the patient or by influences of noises or the like. In order to grasp the condition of the patient, it is important to know the reliability of the measurement value.

In the related art, a trend display of measurement values is performed after a certain amount of noise is eliminated from trend data by a filter or the like, or performed by displaying all the data without using a filter or the like.

As a related art for displaying an electrocardiogram waveform with high reliability in distinction to that with low reliability, there is the following technique. An electrocardiogram waveform which is wirelessly transmitted is received, and the reception intensity is measured. A portion of the electrocardiogram waveform where the reception intensity is lower than a threshold is deemed as an electrocardiogram waveform in which the reliability is lowered by abnormality of the reception signal, and indicated by a line which is thinner than lines for other portions. Therefore, an electrocardiogram waveform with high reliability is displayed in distinction to that with low reliability (for example, see JP-A-2010-57616).

The technique, which is the above former related art, for performing a display after eliminating noises has a problem in that it is difficult to set the constant of the filter, and even actual biological information is eliminated and not displayed. In the case where a filter or the like is not used, there arises a problem in that, when many noises occur, it is very difficult to view the display, and biological information is hardly distinguished.

The technique disclosed in JP-A-2010-57616, which is the above latter related art, has a problem in that biological information in which the reliability is reduced by influences of noises that do not appear as the intensity cannot be displayed in distinction to that with high reliability. Namely, the technique cannot be applied to noises occurring in a process which is performed during a period from the detection of biological information from the patient by a sensor to the wireless transmission of the information. The technique has another problem in that it cannot be applied to a case where biological information which is acquired by means other than wireless transmission is displayed while biological information with high reliability is displayed in distinction to that with low reliability.

SUMMARY

The invention provides an apparatus and biological information displaying method in which a specific measurement value in which the reliability is reduced by influences of various noises, and a specific measurement value with high reliability can be displayed in accurate distinction to each other.

According to an aspect of the invention, there is provided a biological information displaying apparatus comprising: a measuring section which is configured to measure a biological information waveform containing a specific measurement value; a calculating section which is configured to calculate the specific measurement value based on the biological information waveform that is measured by the measuring section in a designated unit time; a determining section which is configured to determine a level of a reliability of the specific measurement value that is calculated by the calculating section, based on the biological information waveform that is measured by the measuring section in the unit time; and a displaying section which is configured to display a trend graph of the specific measurement values while the specific measurement values are distinct according to the level of the reliability that is determined by the determining section. According to an aspect of the invention, there is provided a biological information displaying method comprising: measuring a biological information waveform containing a specific measurement value; calculating the specific measurement value based on the biological information waveform that is measured in the measuring process in a designated unit time; determining a level of a reliability of the calculated specific measurement value based on the biological information waveform that is measured in the unit time; and displaying a trend graph of the specific measurement values while the specific measurement values are distinct according to the determined level of the reliability.

DESCRIPTION OF EMBODIMENTS

Hereinafter, the apparatus and biological information displaying method according to an embodiment of the invention will be described in detail with reference to the drawings.

Figure 1:
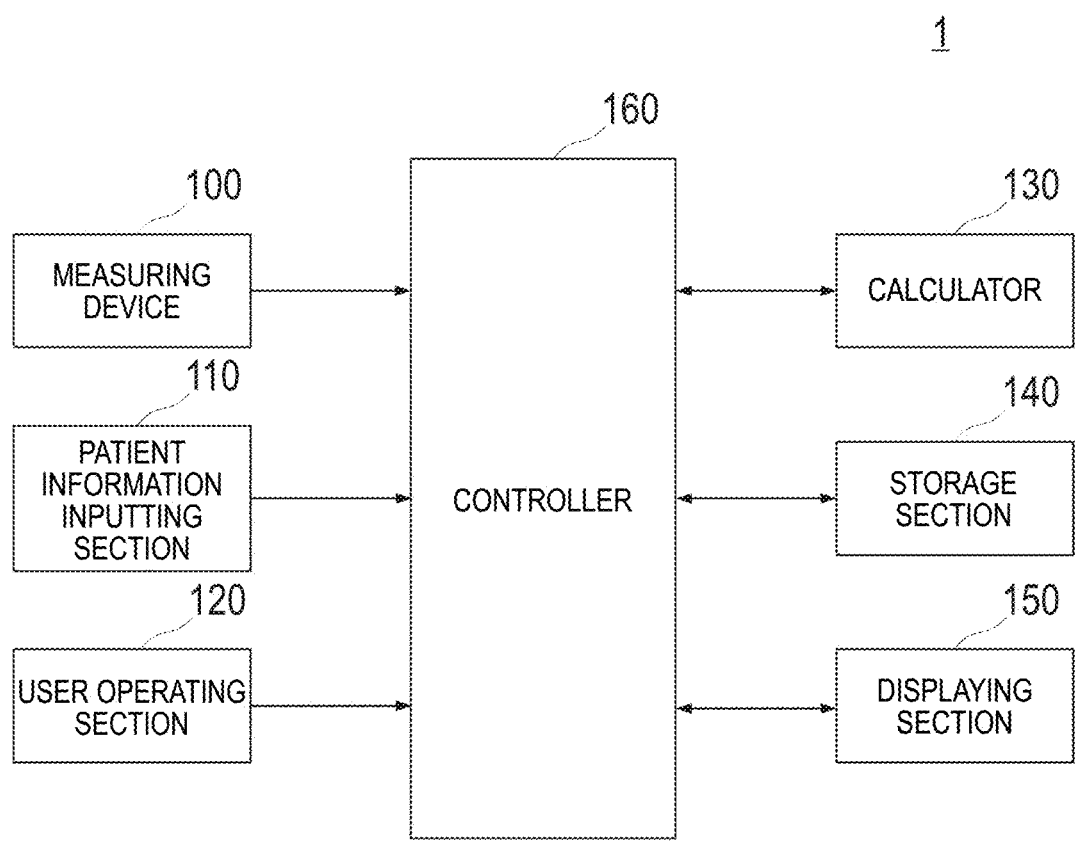
FIG. 1 is a block diagram of a biological information displaying apparatus according to an embodiment of the invention.

FIG. 1 is a block diagram of the biological information displaying apparatus according to the embodiment of the invention. As shown in FIG. 1, the apparatus 1 for displaying biological information according to the embodiment has a measuring device 100, a patient information inputting section 110, a user operating section 120, a calculator 130, a storage section 140, a displaying section 150, and a controller 160.

The measuring device 100 constitutes the measuring section, and the calculator 130 and the controller 160 constitute the calculating section and the determining section. The displaying section 150 constitutes the displaying section.

For example, the apparatus 1 for displaying biological information may be configured as an electrocardiograph or a biological information monitor. In the apparatus 1 for displaying biological information, the components other than the measuring device 100 may be configured by a personal computer.

The measuring device 100 measures biological information. The biological information is physiological information which is periodically generated from a living body, such as an electrocardiogram. Alternatively, the biological information may be an invasive blood pressure waveform or a pulse pressure waveform.

In the following description, for the sake of simplicity, it is assumed that the measuring device 100 measures an electrocardiogram as the biological information.

The measuring device 100 may be configured by: electrodes which are to be attached to a plurality of places of the body surface of the patient, and which are used for obtaining an electrocardiogram; an amplifier which amplifies the electrocardiogram; a filter which eliminates noises from the electrocardiogram that is amplified by the amplifier; an AD converter for digitizing the electrocardiogram which is amplified, and from which noises are eliminated; and an interface for transmitting the electrocardiogram to the controller 160.

After the electrodes are attached to the predetermined places of the body surface of the patient, the measuring device 100 measures an electrocardiogram. The measuring device 100 transmits the measured electrocardiogram to the controller 160.

The patient information inputting section 110 is configured by, for example, a keyboard or a touch panel.

When the user operates keys, patient information is input to the patient information inputting section 110. For example, the patient information includes the ID, name, age, and sex of the patient. The patient information inputting section 110 transmits the input patient information to the controller 160.

The user operating section 120 is configured by, for example, a keyboard or a touch panel. The keyboard or touch panel constituting the user operating section 120 may be used also as those constituting the patient information inputting section 110.

Through the user operating section 120, the user inputs a designation of a threshold for a reliability index which is calculated based on the measured electrocardiogram waveform (biological information waveform). The reliability of specific measurement values of the electrocardiogram is determined according to the degree of the reliability index. The reliability index is a numerical value for determining the reliability of specific measurement values, and, for example, the standard deviation of specific measurement values in a designated period of time, indicating statistical dispersion of measured specific measurement values. The reliability index may be statistical dispersion of fluctuation of an electrocardiogram waveform in a portion where the baseline is appearable in the electrocardiogram waveform (such as the T(U)P interval or the PQ interval) and in an arbitral time zone, such as the degree, the standard deviation, or the like. The user designates the contents of the reliability index through the user operating section.

Through the user operating section 120, the user inputs a designated period of time (hereinafter, referred to simply as "designated time") which, in a trend graph of specific measurement values displayed on the displaying section 150, is used for designating one of the specific measurement values plotted on the graph, by means of a time period. As described later, electrocardiogram waveforms which are used as the basis for calculating specific measurement values in the designated time are displayed together with the trend graph of specific measurement values on the displaying section 150.

Through the user operating section 120, the user inputs a designation of a unit time period (hereinafter, referred to simply as "unit time") for enabling the measuring device 100 to measure electrocardiogram waveforms of a plurality of beats of the electrocardiogram which, in the trend graph of specific measurement values, are used as the basis for calculating specific measurement values to be plotted on the graph. For example, the designation of the unit time may be that of one minute. In the following description, for the sake of simplicity, it is assumed that the unit time is one minute.

The user operating section 120 transmits various designations which are input by the user, and which include the above-described designations, to the controller 160.

The calculator 130 may be configured by a CPU (Central Processing Unit), a RAM (Random Access Memory), and an HDD (Hard Disk Drive).

The calculator 130 calculates specific measurement values based on electrocardiogram waveforms measured by the measuring device 100.

As specific measurement values, for example, the calculator 130 may calculate the PQ interval, QRS width, QT interval, QTc interval, P wave width, T wave width, and U wave width which are indexes related to the time of an electrocardiogram waveform. The QTc interval is a QT interval which has undergone correction for eliminating an influence caused by the RR interval. The correction is performed in consideration that also the QT interval is increased by an increase of the RR interval.

As specific measurement values, for example, the calculator 130 may calculate the P wave amplitude, Q wave amplitude, R wave amplitude, S wave amplitude, T wave amplitude, U wave amplitude, or ST level which are indexes related to the amplitude of an electrocardiogram waveform.

In the case where the PQ interval is to be calculated as a specific measurement value, for example, the calculator 130 calculates the time period from beginning of the P wave to that of the Q wave, whereby the PQ interval can be calculated.

The calculator 130 further calculates the representative value of specific measurement values based on electrocardiogram waveforms of a plurality of beats from which specific measurement values are measured in the unit time. In accordance with the designation of the unit time which is designated by the user through the user operating section 120, the calculator 130 calculates the representative value of specific measurement values based on the electrocardiogram waveforms of a plurality of beats which are measured in the unit time. Namely, the calculator 130 calculates the representative value of specific measurement values from a waveform (hereinafter, referred to simply as "representative waveform") based on the electrocardiogram waveforms of a plurality of beats which are measured in the unit time. The representative waveform is statistically obtained from the electrocardiogram waveforms of a plurality of beats which are measured in the unit time, and, for example, a waveform which is obtained by arithmetically averaging electrocardiogram waveforms of a plurality of beats. The representative waveform may be a waveform which provides the median value of the potentials of samples of the electrocardiogram waveforms of a plurality of beats. A specific measurement value which is plotted on the trend graph of specific measurement values is the representative value of specific measurement values.

In the case where specific measurement values are calculated from electrocardiograms in a plurality of places of the human body (hereinafter, referred to simply as "plurality of leads") such as a 12-lead electrocardiogram, the calculator 130 sets an average or median value which is obtained by applying a statistical process to specific measurement values calculated respectively from representative waveforms, as the representative value of the specific measurement values. Alternatively, a maximum value which is defined as the interval between the earliest one of start timings the latest one of end timings of waveform widths defining specific measurement values appearing respectively in representative waveforms may be set as the representative value.

The calculator 130 calculates the reliability index which is designated by the user. In the case where the reliability index which is designated by the user is dispersion of the specific measurement values, the calculator 130 may calculate statistical dispersion such as the standard deviation or the root-mean-square which is obtained by applying a statistical process to specific measurement values of electrocardiogram waveforms of a plurality of beats which are measured in the unit time, as the reliability index. In the case where the reliability index which is designated by the user is the degree of fluctuation in a portion where the baseline is appearable in the electrocardiogram waveform and in an arbitral time zone (for example, the interval between the P wave and the Q wave), the calculator can apply a statistical process to electrocardiogram waveforms in the time zone, and calculate the degree of the fluctuation indicating a statistical dispersion, the standard deviation of the fluctuation, or the like, as the reliability index.

In the case where dispersion of specific measurement values is to be calculated, the calculator 130 may calculate dispersion of specific measurement values based on statistical dispersion of specific measurement values of each beats and in a unit time.

The calculator 130 calculates a determined value which is a statistical value in a predetermined time period, based on the representative value of continuous specific measurement values in which, among the calculated representative values of specific measurement values, the reliability is determined to be high, by the controller 160. The determined value may be the average value (moving average), median value, minimum value, or maximum value in the predetermined time period, or the like. In the following description, for the sake of simplicity, it is assumed that a statistical value in a predetermined time period is the moving average.

The storage section 140 may be configured by the HDD.

The storage section 140 stores various measurement values such as measured electrocardiograms, specific measurement values, and the dispersion of the specific measurement values. The storage section 140 further stores patient information and various designations by the user such as the designation of the threshold. The storage section 140 stores a control program which is to be executed by the controller 160 to control the components of the apparatus 1 for displaying biological information.

The displaying section 150 may be configured by a liquid crystal displaying device.

According to determination by the controller 160, the displaying section 150 displays a trend graph of specific measurement values calculated by the calculator 130 while specific measurement values with high reliability are displayed in distinction to those with low reliability. The displaying section 150 can display the moving average of specific measurement values with high reliability, with superimposed on the trend graph of specific measurement values.

The displaying section 150 displays a representative waveform which is used as the basis for calculating specific measurement values in the designated time of specific measurement values displayed in the trend graph of specific measurement values.

The displaying section 150 can display relationships among specific measurement values in the designated time of specific measurement values displayed in the trend graph of specific measurement values, the moving average of the specific measurement values in the designated time, and dispersion of the specific measurement values in the designated time.

While corresponding with the representative waveform which is used as the basis for calculating specific measurement values in the designated time of specific measurement values displayed in the trend graph of specific measurement values, the displaying section 150 can display level relationships of specific measurement values which are calculated based on the representative waveform. The displaying section 150 can display the level relationships in the form of a graph or numerical values. When the level relationships of specific measurement values are displayed in the form of numerical values, the displaying section 150 can display the specific measurement values while the maximum and minimum values are displayed in a distinguishable manner.

In the case where the median value of specific measurement values calculated based on representative waveforms which are measured respectively by a plurality of leads is designated as the representative value by the user, the displaying section 150 can display at least one of the representative waveform which provides the median value, and the median value in a distinguishable manner.

The displaying section 150 can display the representative waveform with superimposed on a display showing the starting and ending timings of the time width defining the representative value.

In the case where the reliability index is calculated based on fluctuation in an arbitral time zone in which the baseline is appearable in the electrocardiogram waveform, the displaying section 150 may further display the value of the reliability index in the designated time.

The controller 160 may configured by the CPU and the RAM.

In accordance with the control program which is stored in the storage section 140, the controller 160 controls the components of the apparatus 1 for displaying biological information.

The controller 160 transmits and stores the electrocardiogram, patient information, and various designations by the user such as the designation of the threshold which are received from the measuring device 100, the patient information inputting section 110, and the user operating section 120, to the storage section 140.

The controller 160 determines the level of the reliability of the specific measurement value calculated by the calculator 130. If the reliability index calculated by the calculator 130 does not exceed the threshold designated by the user, the controller 160 determines that the specific measurement value from which the reliability index is calculated is a specific measurement value with high reliability. If the reliability index exceeds the threshold designated by the user, the controller 160 determines that the specific measurement value from which the reliability index is calculated is a specific measurement value with low reliability. Alternatively, a plurality of thresholds may be set, and the degree of the reliability may be set in three or more stages.

A display screen which is displayed on the displaying section 150 of the apparatus 1 for displaying biological information will be described with reference to FIGS. 2 to 5C. The determination of which one of FIGS. 2 to 5C is to be displayed as the display screen is performed by designation by the user through the user operating section 120.

Figure 2:
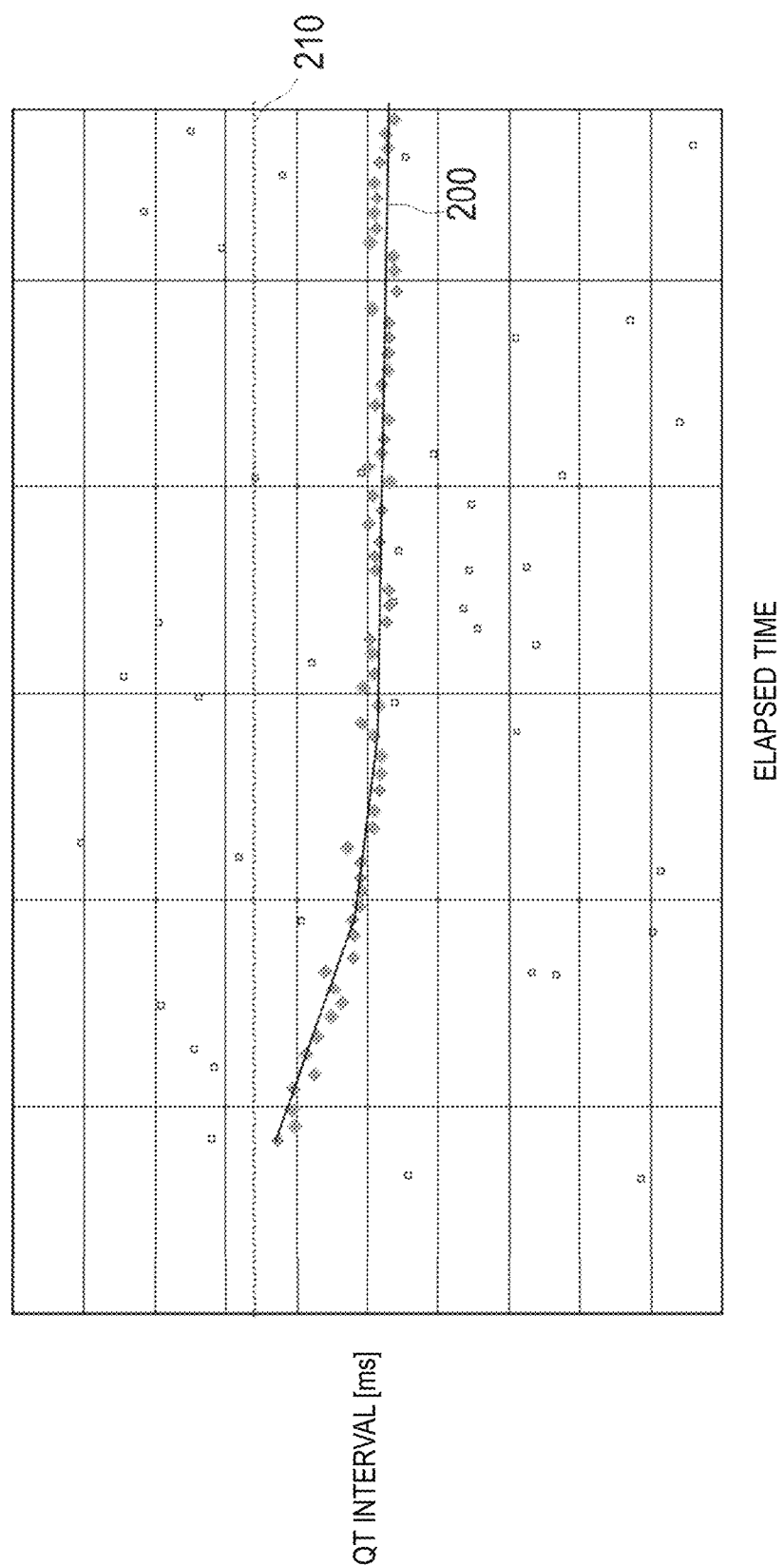
FIG. 2 illustrates a trend graph of specific measurement values which is displayed in the biological information displaying apparatus according to the embodiment of the invention.

FIG. 2 is a view illustrating a trend graph of specific measurement values which is displayed in the biological information displaying apparatus according to the embodiment.

The abscissa of the graph of FIG. 2 indicates the elapsed time in the measurement of specific measurement values. The intervals of plots indicating measured values of the measured specific measurement value are equal to one minute. The ordinate of the graph of FIG. 2 indicates a measured value of the QT interval which is the specific measurement value.

The value plotted on the graph of FIG. 2 is the representative value of the specific measurement value, and the average value of the QT interval which is calculated based on representative waveforms of the leads of a 12-lead electrocardiogram. The value which is to be plotted on the trend graph of specific measurement values may be the median value of specific measurement values calculated from representative waveforms of the leads of the 12-lead electrocardiogram. The value which is to be plotted may be a value which is defined as the interval between the earliest one of start timings and the latest one of end timings of waveform widths defining specific measurement values appearing in representative waveforms of the leads of a 12-lead electrocardiogram.

In the plots of the graph of FIG. 2, the solid rhombus plots are plots of specific measurement values with high reliability, and the hollow square plots are plots of specific measurement values with low reliability. When specific measurement values with high reliability are displayed in distinction to those with low reliability as described above, the user can infer the true trend and change of specific measurement values in a trend graph of the specific measurement values, from specific measurement values with high reliability while knowing specific measurement values with low reliability.

As indicated by the solid curve in FIG. 2, the moving average 200 of specific measurement values with high reliability in the calculated specific measurement values is superimposed in the trend graph of specific measurement values. When the moving average 200 of specific measurement values with high reliability is superimposed in a trend graph of specific measurement values in this way, the user can infer more easily and clearly the true trend and change of specific measurement values. As described above, the moving average may be the median value, minimum value, or maximum value of representative values in the predetermined time period.

As indicated by the broken line 210 in FIG. 2, a line which will be used by the user as a measurement value guide for specific measurement values may be superimposed in a trend graph of specific measurement values in a manner that the line can be changed by the user.

Figures 3A, 3B, 3C:
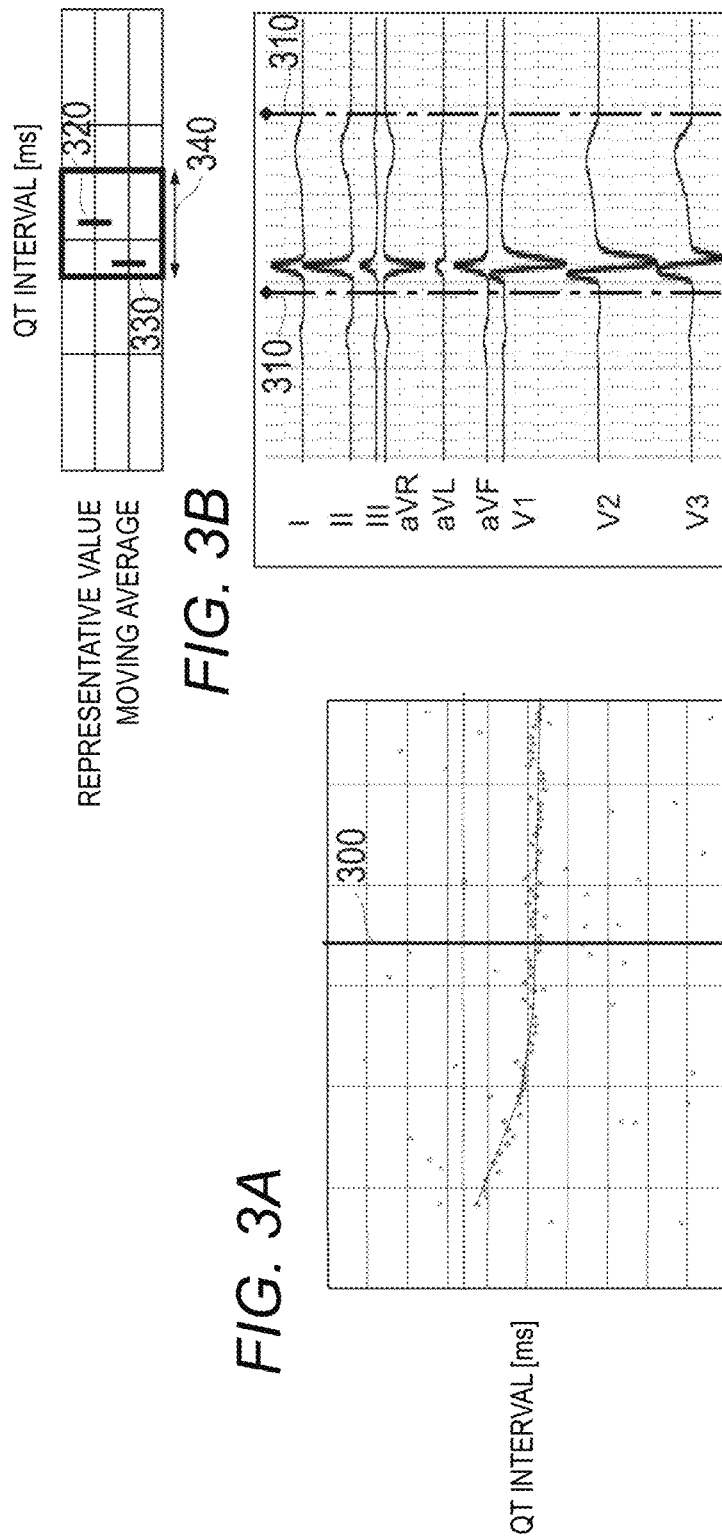
FIG. 3A illustrates a trend graph of specific measurement values which are simultaneously displayed in the biological information displaying apparatus according to the embodiment of the invention.
FIG. 3B illustrates biological information waveforms which are used as a base for calculation of the specific measurement values in a designated period of time.
FIG. 3C illustrates relationships between a level relationship graph of measured values of the specific measurement values in the designated period of time, the moving average, and dispersion of the specific measurement values.

FIG. 3A is a trend graph of specific measurement values which are simultaneously displayed in the biological information displaying apparatus according to the embodiment, FIG. 3B illustrates waveforms which are used as the basis for calculation of the specific measurement values in the designated time, and FIG. 3C is a view illustrating relationships between measured values of the specific measurement values in the designated time, the moving average, and dispersion of the specific measurement values. The QT intervals are displayed as specific measurement values in FIGS. 3A, 3B, and 3C.

FIG. 3A illustrates a trend graph of the QT intervals which is displayed in the biological information displaying apparatus.

The QT interval which is plotted in the graph of FIG. 3A is the representative value of the QT intervals, and a value which is defined as the interval between the earliest one of start timings and the latest one of end timings of leads defining the QT intervals appearing in representative waveforms (see FIG. 3B) of the leads of a 12-lead electrocardiogram.

FIG. 3A further illustrates a cursor 300 indicating the time designated by the user, in the trend graph of the QT intervals. The position of the cursor 300 which is shown as the designated time in FIG. 3A can be changed in accordance with a change of the designated time performed by the user.

FIG. 3B illustrates the representative waveforms which are used as the basis for calculating the QT interval in the designated time. The symbols which are displayed on the left sides of the representative waveforms indicate the lead names of the leads of a 12-lead electrocardiogram, respectively.

The waveforms of the leads of a 12-lead electrocardiogram shown in FIG. 3B are representative waveforms of the respective leads, and waveforms which are obtained by arithmetically averaging electrocardiogram waveforms of a plurality of beats measured in the unit time. In FIG. 3B, lines 310 indicating respectively the earliest one of start timings and the latest one of end timings of waveform widths defining the QT interval appearing in these waveforms are shown.

FIG. 3C illustrates relationships between measured values of the QT intervals in the designated time, the moving average in the designated time, and dispersion of the QT intervals.

As shown in FIG. 3C, the level relationships of the measurement values 320 of the QT intervals in the designated time, and the moving average 330 are shown by plotting them in a graph in which the value becomes larger as proceeding toward the upper right side of the graph. The values which are indicated as measurement values of the QT intervals are the representative values of the QT intervals which are plotted in FIG. 3A, and those which are indicated as moving averages are values of the moving average displayed in FIG. 3A.

The dispersion of the QT intervals can be indicated as the standard deviation of the QT intervals of each beats which are calculated in the unit time during the designated time. The standard deviation which is the dispersion of the QT intervals is indicated as the size 340 of the lateral width of the large square in FIG. 3C. Preferably, the color of the vertical thick solid line which is indicated as plots of the measurement values 320 of the QT intervals is changed correspondingly with the level of the reliability of the QT intervals. The level of the reliability is determined by whether the value of the standard deviation which is the dispersion of the QT intervals exceeds the threshold designated by the user or not.

Figure 4C:
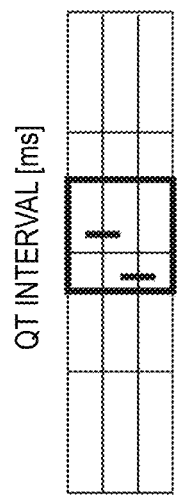
FIG. 4C illustrates relationships between a level relationship graph of measured values of the specific measurement values in the designated period of time, the moving average, and dispersion of the specific measurement values.
Figure 4B:
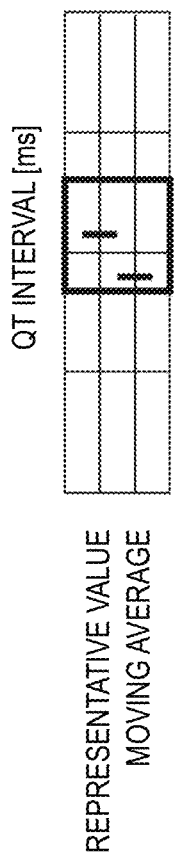
FIG. 4B illustrates biological information waveforms which are used as a basis for calculation of the specific measurement values in a designated period of time, and a graph of level relationships between specific measurement values of leads.
Figure 4B:
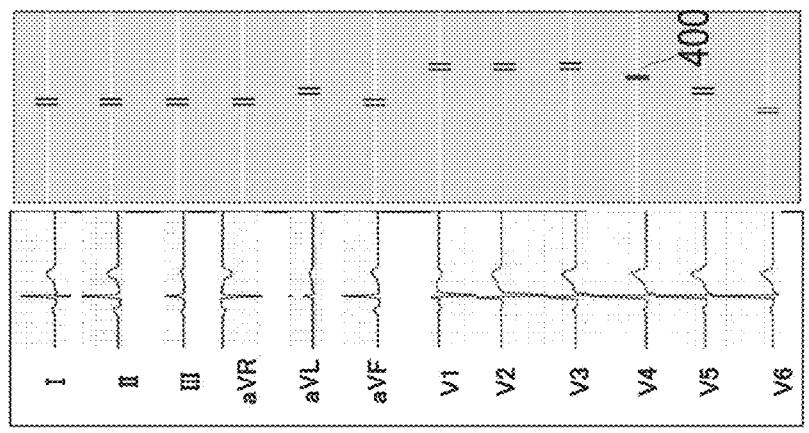
Figure 4A:
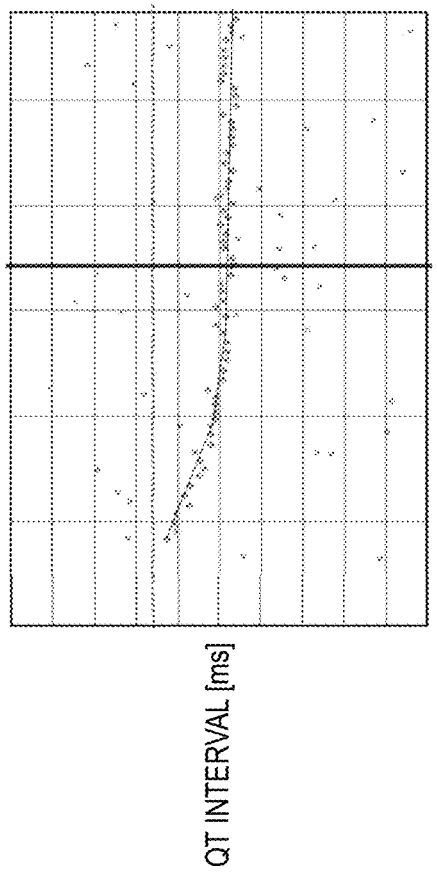
FIG. 4A illustrates a trend graph of specific measurement values which are simultaneously displayed in the biological information displaying apparatus according to the embodiment of the invention.

FIG. 4A is a trend graph of specific measurement values which are simultaneously displayed in the biological information displaying apparatus according to the embodiment, FIG. 4B illustrates representative waveforms which are used as the basis for calculation of the specific measurement values in the designated time, and a graph of level relationships between specific measurement values, and FIG. 4C is a view illustrating relationships between measured values of the specific measurement values in the designated time, the moving average, and dispersion of the specific measurement values. Similarly with FIGS. 3A, 3B, and 3C, the QT intervals are displayed as specific measurement values in FIGS. 4A, 4B, and 4C.

FIG. 4C is a graph which is similar to that of FIG. 3C, and therefore its description is omitted.

FIG. 4A illustrates a trend graph of the QT intervals which is displayed in the biological information displaying apparatus.

The QT intervals which are plotted in the graph of FIG. 4A are the representative values of the QT values, and the median values of the QT intervals which are calculated from representative waveforms of the leads of a 12-lead electrocardiogram.

FIG. 4B illustrates representative waveforms which are used as the basis for calculation of the QT intervals in the designated time, and a graph of level relationships of the QT intervals.

The left figure of FIG. 4B is a view showing the representative waveforms which are used as the basis for calculation of the QT intervals in the designated time. The symbols which are displayed on the left sides of the representative waveforms indicate the lead names of the leads of a 12-lead electrocardiogram, respectively.

The representative waveforms of the leads of a 12-lead electrocardiogram shown in the left figure of FIG. 4B are representative waveforms which are measured in the unit times for the respective leads, and waveforms which are obtained by arithmetically averaging electrocardiogram waveforms of the plurality of beats.

The right figure of FIG. 4B is a graph showing level relationships of measured values of the QT intervals of leads corresponding to the representative waveforms of the leads of the left figure of FIG. 4B. The level relationships of the measured values of the QT intervals of the leads are shown by plotting the measured values of the QT intervals by using vertical short double lines in a graph in which the value becomes larger as proceeding toward the upper right side of the graph.

As described above, the representative values plotted as the QT intervals in FIG. 4A are the median values of the QT intervals which are calculated from representative waveforms of the leads of a 12-lead electrocardiogram. In the right figure of FIG. 4B, therefore, the median values of the QT intervals which are calculated respectively from representative waveforms of the leads are displayed by plots 400 of thick single lines in a manner distinguishable from other plots. The median values are QT intervals which are calculated from waveforms obtained by arithmetically averaging electrocardiogram waveforms of a plurality of beats measured in the unit time in the V4 channel of the 12 leads. In this case, the representative waveform of the V4 lead which provides the median value may be displayed in a manner distinguishable from other waveforms.

Figure 5C:
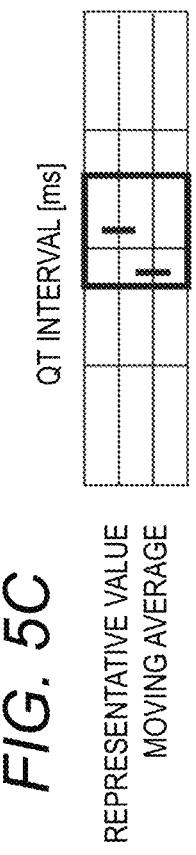
FIG. 5C illustrates relationships between a level relationship graph of measured values of the specific measurement values in the designated period of time, the moving average, and dispersion of the specific measurement values.
Figure 5B:
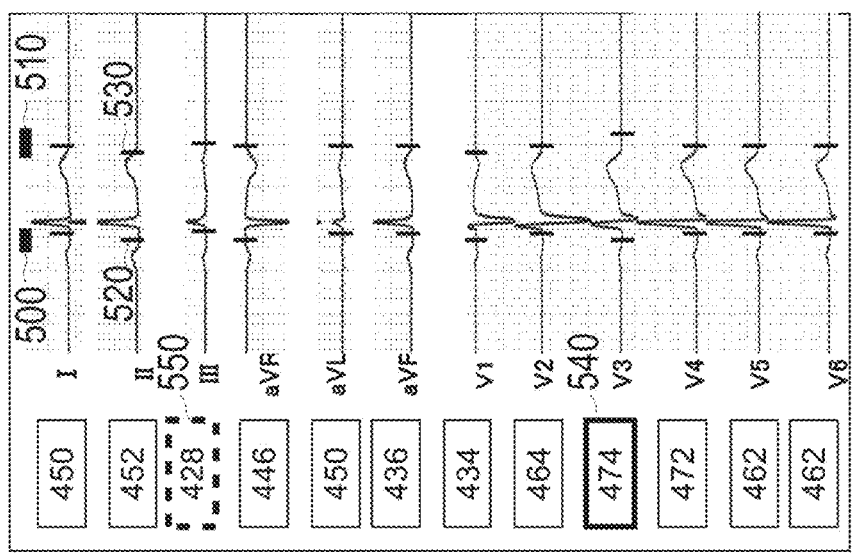
FIG. 5B is a view illustrating biological information waveforms which are used as a basis for calculation of the specific measurement values in a designated period of time, and the numerical values of the specific measurement values.
Figure 5A:
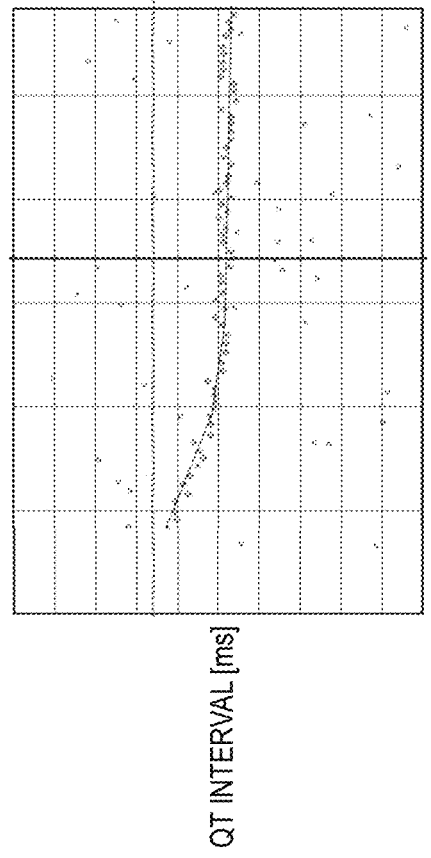
FIG. 5A illustrates a trend graph of specific measurement values which are simultaneously displayed in the biological information displaying apparatus according to the embodiment of the invention.

FIG. 5A is a trend graph of specific measurement values which are simultaneously displayed in the biological information displaying apparatus according to the embodiment, FIG. 5B is a view illustrating level relationships between representative waveforms and the values of the specific measurement values, and FIG. 5C is a view illustrating relationships between measured values of the specific measurement values in the designated time, the moving average, and dispersion of the specific measurement values. Similarly with FIGS. 3A, 3B, 3C, 4A, 4B, and 4C, the QT intervals are displayed as specific measurement values in FIGS. 5A, 5B, and 5C.

FIGS. 5A and 5C are graphs which are similar to those of FIGS. 3A and 3C, and therefore their description is omitted.

FIG. 5B illustrates representative waveforms which are used as the basis for calculation of the QT intervals in the designated time, and the values of the QT intervals.

The right figure of FIG. 5B illustrates representative waveforms which are used as the basis for calculation of the QT intervals in the designated time. The symbols which are displayed on the left sides of the representative waveforms indicate the lead names of the leads of a 12-lead electrocardiogram, respectively.

The representative waveforms of the leads of the 12-lead electrocardiogram which are shown in the right portion of FIG. 5B are representative waveforms which are measured in the unit times for the respective leads, and waveforms which are obtained by arithmetically averaging electrocardiogram waveforms of the plurality of beats.

In the right portion of FIG. 5B, the interval between the earliest one of start timings and the latest one of the start timings of waveform widths defining the QT intervals of representative waveforms of the leads is indicated by the lateral thick line 500, and the start timing 520 is indicated in the representative waveforms of the leads. Moreover, the interval between the earliest one of end timings and the latest one of the end timings of waveform widths defining the QT intervals appearing in the representative waveforms of the leads is indicated by the lateral thick line 510, and the end timing 530 is indicated in the representative waveforms of the leads.

In the left portion of FIG. 5B, the QT intervals which are measured by the leads in the right portion of FIG. 5B, and which correspond to the representative waveforms are indicated by numerical values. In the left portion of FIG. 5B, the maximum value of the measured values of the QT intervals of the leads is enclosed by the thick solid-line frame, and the minimum value is enclosed by the thick broken-line frame. Therefore, the user can know the leads in which the maximum and minimum values of the QT intervals are measured, at a glance, and more clearly grasp the QT intervals measured in the leads, in the form of numerical values.

Figure 6:
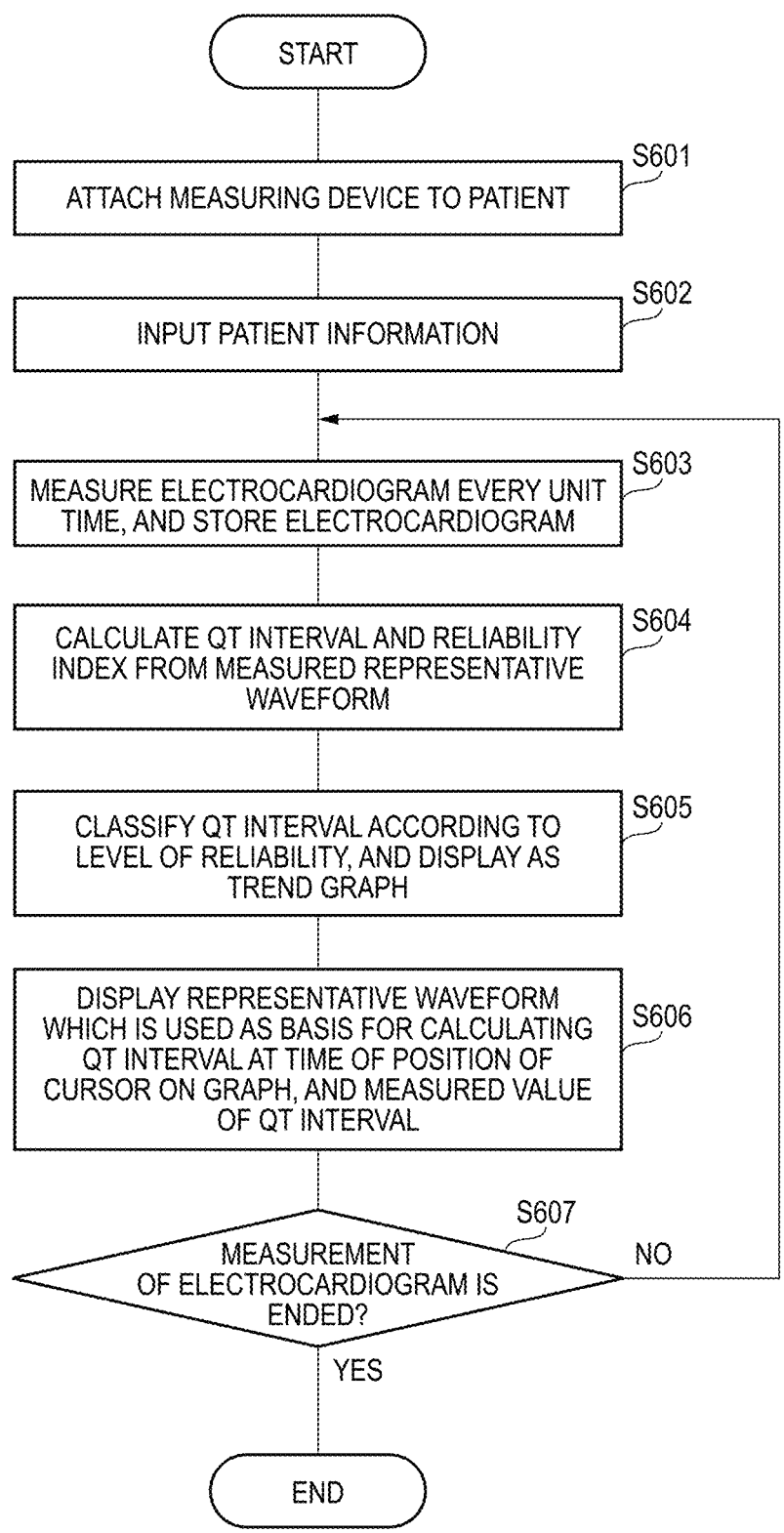
FIG. 6 is a flowchart of a biological information displaying method according to the embodiment of the invention.

FIG. 6 is a flowchart of a biological information displaying method according to the embodiment. The flowchart can be performed by the apparatus 1 for displaying biological information according to the embodiment.

The user attaches the measuring device 100 to the patient (S601), and inputs patient information through the patient information inputting section 110 (S602).

The controller 160 controls the measuring device 100 to measure an electrocardiogram every unit time which is designated by the user, and stores the measured electrocardiogram in the storage section 140 (S603).

The controller 160 controls the calculator 130 to calculate the representative value of the QT intervals from the representative waveforms which are measured in the unit times, and also to calculate the standard deviation of the QT intervals functioning as the reliability index, based on the electrocardiogram waveforms (S604).

The controller 160 sets a QT interval in which the calculated standard deviation of the QT interval does not exceed the threshold designated by the user, as a QT interval with high reliability, and a QT interval in which the standard deviation exceeds the threshold, as a QT interval with low reliability, and controls the displaying section 150 to display them in distinction from each other, as a trend graph on the displaying section 150 (S605).

The controller 160 causes the representative waveform which is used as the basis for calculating the QT interval at the time of the position of the cursor indicating the designated time designated by the user, and a measured value of the QT interval to be displayed together with the trend graph of QT intervals (S606).

The controller 160 repeats steps S601 to S606 until the measurement of the electrocardiogram is ended (S607).

The apparatus and biological information displaying method according to the embodiment of the invention have been described. The embodiment achieves the following effects.

A specific measurement value is calculated from a measured electrocardiogram waveform, and the reliability of the calculated specific measurement value is determined based on the electrocardiogram waveform. Specific measurement values are displayed as a trend graph of specific measurement values while specific measurement values with high reliability are displayed in distinction to those with low reliability. Therefore, the reliability of the measured specific measurement value is determined based on the electrocardiogram waveform, whereby a specific measurement value in which the reliability is reduced by influences of various noises, and a specific measurement value with high reliability can be displayed in accurate distinction to each other.

According to the degree of dispersion of specific measurement values which are calculated based on electrocardiogram waveforms that are measured in a designated unit time, the reliability of the specific measurement values is determined. Therefore, it is possible to display a trend graph of specific measurement values in a manner that the level of the reliability is distinguishable more surely and accurately.

Based on the degree of fluctuation in an arbitral time zone of an electrocardiogram waveform, the reliability of the specific measurement value which is calculated from the electrocardiogram waveform is determined. Therefore, a trend graph of specific measurement values can be displayed in a manner that the level of the reliability is distinguishable more surely and accurately.

The moving average of specific measurement values in which the reliability is determined to be high is displayed superimposedly on a trend graph of specific measurement values. Therefore, the true trend and change of specific measurement values can be inferred more easily and clearly.

The reliability of a specific measurement value is determined according to representative values based on electrocardiogram waveforms of leads, or a waveform based on representative waveforms of the leads. Even in the case where electrocardiogram waveforms are measured in a plurality of leads, therefore, the reliability of a specific measurement value can be determined comprehensively and accurately.

A specific measurement value is calculated based on a designated representative waveform, and its reliability is determined. Therefore, the reliability of a specific measurement value can be determined more simply and accurately.

The representative value is set to at least one of: the average value and median value of specific measurement values which are calculated in respective leads based on electrocardiogram waveforms or the representative waveform; and a value which is defined as the interval between the earliest one of start timings and the latest one of end timings of waveform widths defining specific measurement values appearing in the electrocardiogram waveforms or the representative waveform. Therefore, the reliability of a specific measurement value can be determined flexibly and adequately.

An electrocardiogram waveform or representative waveform which is used as the basis for calculating specific measurement values in the designated time of specific measurement values displayed in a trend graph of specific measurement values is displayed together with the trend graph of specific measurement values. Therefore, the reliability of a specific measurement value displayed in the trend graph of specific measurement values can be determined more specifically.

Relationships among specific measurement values in the designated time of specific measurement values displayed in a trend graph of specific measurement values, the moving average of the specific measurement values in the time, and the dispersion of the specific measurement values in the time are displayed together with the trend graph of specific measurement values. Therefore, the reliability of a specific measurement value displayed in the trend graph of specific measurement values can be determined more specifically and adequately.

While corresponding with electrocardiogram waveforms or a representative waveform which is used as the basis for calculating specific measurement values in the designated time of specific measurement values displayed in a trend graph of specific measurement values, level relationships of specific measurement values which are calculated based on the electrocardiogram waveforms or the representative waveform are displayed in the form of a graph or numerical values together with the trend graph of specific measurement values. Therefore, the reliability of a specific measurement value displayed in the trend graph of specific measurement values can be determined more specifically and simply.

In the case where the representative value is designated as the median value of specific measurement values which are calculated based on electrocardiogram waveforms that are measured by a plurality of leads or representative waveform, the electrocardiogram waveforms or the representative waveform and the specific measurement values are displayed in a manner that at least one of the electrocardiogram waveforms or representative waveform which provides the median value, and the median value which is calculated based on the waveforms is distinguishable. Therefore, the reliability of a specific measurement value displayed in the trend graph of specific measurement values can be determined more flexibly and specifically.

In the case where level relationships of specific measurement values are displayed in the form of numerical values, the specific measurement values are displayed while the maximum and minimum values of the values are displayed in a distinguishable manner. Therefore, the reliability of a specific measurement value displayed in the trend graph of specific measurement values can be determined more specifically and adequately.

The electrocardiogram waveforms or the representative waveform is displayed with superimposed on a display showing the starting and ending timings of the time width defining the representative value. Therefore, the reliability of a specific measurement value displayed in the trend graph of specific measurement values can be determined more specifically and correctly. The apparatus and biological information displaying method of the invention are not limited to the above-described embodiment.

Although, in the embodiment, a representative value of specific measurement values is calculated from representative waveforms which are measured in the unit time in the leads of a 12-lead electrocardiogram, a representative value of specific measurement values may be calculated from electrocardiogram waveforms of each beats. In this case, the reliability of a specific measurement value may be determined while the reliability index is set as the degree of fluctuation of an electrocardiogram waveform in an arbitral time zone in which the baseline is appearable in the electrocardiogram waveform, or the standard deviation of the fluctuation.

In the embodiment, it has been described that the biological information displaying apparatus is controlled in accordance with the control program. Alternatively, a part or all of the control program may be replaced with hardware such as a custom LSI (Large Scale Integrated Circuit). In the embodiment, examples of the reliability index are the degree of fluctuation of an electrocardiogram waveform in a time zone in which the baseline is appearable in the electrocardiogram waveform, and the standard deviation of the fluctuation. Alternatively, the degree of fluctuation of an electrocardiogram waveform in a time zone other than that in which the baseline is appearable in the electrocardiogram waveform, or the standard deviation of the fluctuation may be used as the reliability index.

According to the invention, a specific measurement value is calculated from a measured biological information waveform, and the reliability of the calculated specific measurement value is determined based on the biological information waveform. Specific measurement values are displayed as a trend graph of specific measurement values while specific measurement values are distinct depending on the reliability. The reliability of the calculated specific measurement value is determined based on the biological information waveform which is used as the basis for calculating the specific measurement value. Therefore, a specific measurement value in which the reliability is reduced by influences of various noises, and a specific measurement value with high reliability can be displayed in accurate distinction to each other.

What is claimed is:

1. A biological information displaying apparatus comprising:
   a measuring circuit which is configured to measure a biological information waveform containing a specific measurement value;
   at least one computer which is configured to calculate the specific measurement value based on the biological information waveform that is measured by the measuring circuit in a designated unit time;
   the at least one computer being further configured to determine a level of a reliability of the specific measurement value, based on the biological information waveform that is measured by the measuring circuit in the unit time; and
   a display which is configured to display a trend graph of the specific measurement values while the specific measurement values are distinct according to the level of the reliability that has been determined,
   wherein the at least one computer determines the level of reliability according to a condition which is designated with respect to dispersion of the specific measurement values based on the respective biological information waveforms that are measured by the measuring circuit in the designated unit time, and
   wherein the designated condition is a condition that a statistical dispersion of the specific measurement values that are calculated by the at least one computer based on the respective biological information waveforms that are measured by the measuring circuit in the designated unit time is equal to or smaller than a designated threshold.

2. The biological information displaying apparatus according to claim 1, wherein a statistical value of the specific measurement values in which the reliability is determined to be high by the at least one computer, in a predetermined time period is displayed superimposedly on the trend graph of the specific measurement values.

3. The biological information displaying apparatus according to claim 1, wherein the specific measurement value in which the level of the reliability is determined is a representative value which is calculated based on the biological information waveforms that are respectively measured by the measuring circuit in a plurality of places of a human body, or a waveform based on biological information waveforms of a plurality of beats which are respectively measured by the measuring circuit in the designated unit time in the plurality of places of the human body.

4. The biological information displaying apparatus according to claim 3, wherein the waveform based on the biological information waveforms of the plurality of beats is a waveform which is obtained by arithmetically averaging the electrocardiogram waveforms of the plurality of beats, or a median value.

5. The biological information displaying apparatus according to claim 3, wherein the representative value is at least one of: an average value or a median value of the specific measurement values which are calculated respectively in the plurality of places of the human body based on the biological information waveform, or the waveform based on the biological information waveforms of the plurality of beats; and a value which is defined as an interval between an earliest one of start timings and a latest one of end timings of waveform widths defining the specific measurement values appearing in the biological information waveform, or the waveform based on the biological information waveforms of the plurality of beats.

6. The biological information displaying apparatus according to claim 3, wherein the display further displays the biological information waveform or the waveform based on the biological information waveforms of the plurality of beats, which is used as a basis for calculating the specific measurement value in a designated time, of the specific measurement values displayed in the trend graph of the specific measurement values.

7. The biological information displaying apparatus according to claim 6, wherein, while corresponding with the biological information waveform or the waveform based on the biological information waveforms of the plurality of beats, which is used as the basis for calculating the specific measurement value in the designated time, of the specific measurement values displayed in the trend graph of the specific measurement values, the display further displays level relationships of the specific measurement values which are calculated based on the biological information waveform or the waveform based on the biological information waveforms of the plurality of beats, in a form of a graph or numerical values.

8. The biological information displaying apparatus according to claim 7, wherein, in a case where the level relationships of the specific measurement values are displayed in the form of the numerical values, the display displays the specific measurement values in a manner that maximum and minimum values of the numerical values are distinguishable.

9. The biological information displaying apparatus according to claim 7, wherein the display displays the biological information waveform or the waveform based on the biological information waveforms of the plurality of beats, with superimposed on a display showing starting and ending timings of a time width defining the representative value.

10. The biological information displaying apparatus according to claim 2, wherein the display further displays a relationship among: the specific measurement value in a designated time, of the specific measurement values displayed in the trend graph of the specific measurement values; a statistical value of the specific measurement values during a predetermined time period in the designated time; and dispersion of the specific measurement values in the designated time.

11. The biological information displaying apparatus according to claim 10, wherein, in a case where the representative value is designated as a median value of the specific measurement values which are calculated based on the biological information waveforms that are measured in a plurality of places of a human body, or a waveform based on the biological information waveforms of a plurality of beats, the display displays the biological information waveforms or the waveform based on the biological information waveforms of the plurality of beats, and the specific measurement value in a manner that at least one of the biological information waveform which provides the median value, the waveform based on the biological information waveforms of the plurality of beats, and the median value which is calculated based on these waveforms is distinguishable.

12. A biological information displaying method comprising:
measuring a biological information waveform containing a specific measurement value;
calculating the specific measurement value based on the biological information waveform that is measured in the measuring process in a designated unit time;
determining a level of a reliability of the calculated specific measurement value based on the biological information waveform that is measured in the unit time; and
displaying a trend graph of the specific measurement values while the specific measurement values are distinct according to the determined level of the reliability, wherein, in the determining process, when dispersion of the specific measurement values which are respectively calculated in the calculating process based on the respective biological information waveforms that are measured in the measuring process in the designated unit time satisfies a designated condition, it is determined that the reliability is high, and when the dispersion does not satisfy the condition, it is determined that the reliability is low, and
wherein the designated condition is a condition that a statistical dispersion of the specific measurement values that are calculated in the calculating process based on the respective biological information waveforms that are measured in the measuring process in the designated unit time is equal to or smaller than a designated threshold.

13. A biological information displaying method comprising:
measuring a biological information waveform containing a specific measurement value;
calculating the specific measurement value based on the biological information waveform that is measured in the measuring process in a designated unit time;
determining a level of a reliability of the calculated specific measurement value based on the biological information waveform that is measured in the unit time; and
displaying a trend graph of the specific measurement values while the specific measurement values are distinct according to the determined level of the reliability, wherein, in the determining process, it is determined that the reliability of the specific measurement value which is calculated in the calculating process based on the biological information waveform in which a degree of fluctuation of the biological information waveform in an arbitrary time zone satisfies a designated condition is high, and it is determined that the reliability of the specific measurement value which does not satisfy the condition is low, and
wherein the designated time zone for the biological information waveform is an arbitral time zone in which a baseline is appearable in the biological information waveform.

14. A biological information displaying method comprising:
measuring a biological information waveform containing a specific measurement value;
calculating the specific measurement value based on the biological information waveform that is measured in the measuring process in a designated unit time;
determining a level of a reliability of the calculated specific measurement value based on the biological information waveform that is measured in the unit time; and
displaying a trend graph of the specific measurement values while the specific measurement values are distinct according to the determined level of the reliability,
wherein a statistical value of specific measurement values in which the reliability is determined to be high in the determining process, in a predetermined time period is displayed superimposedly on the trend graph of the specific measurement values.

15. The biological information displaying method according to claim 14, wherein, in the displaying process, further displaying a relationship among: the specific measurement value in a designated time, of the specific measurement values displayed in the trend graph of the specific measurement values; a statistical value of the specific measurement values during a predetermined time period in the designated time; and dispersion of the specific measurement values in the designated time.

16. The biological information displaying method according to claim 15, wherein, in the displaying process, in a case where the representative value is designated as a median value of the specific measurement values which are calculated based on the biological information waveforms that are measured in a plurality of places of a human body, or a waveform based on the biological information waveforms of a plurality of beats, displaying the biological information waveforms or the waveform based on the biological information waveforms of the plurality of beats, and the specific measurement value in a manner that at least one of the biological information waveform which provides the median value, the waveform based on the biological information waveforms of the plurality of beats, and the median value which is calculated based on these waveforms is distinguishable.

17. A biological information displaying method comprising:
measuring a biological information waveform containing a specific measurement value;
calculating the specific measurement value based on the biological information waveform that is measured in the measuring process in a designated unit time;
determining a level of a reliability of the calculated specific measurement value based on the biological information waveform that is measured in the unit time; and
displaying a trend graph of the specific measurement values while the specific measurement values are distinct according to the determined level of the reliability,
wherein the specific measurement value in which the level of the reliability is determined in the determining process is a representative value which is calculated in the calculating process based on the biological information waveforms that are respectively measured in the measuring process in a plurality of places of a human body, or a waveform based on biological information waveforms of a plurality of beats which are respectively measured in the measuring process in the designated unit time in the plurality of places of the human body, and
wherein the waveform based on the biological information waveforms of the plurality of beats is a waveform which is obtained by arithmetically averaging the electrocardiogram waveforms of the plurality of beats, or a median value.

18. A biological information displaying method comprising:
measuring a biological information waveform containing a specific measurement value;
calculating the specific measurement value based on the biological information waveform that is measured in the measuring process in a designated unit time;
determining a level of a reliability of the calculated specific measurement value based on the biological information waveform that is measured in the unit time; and
displaying a trend graph of the specific measurement values while the specific measurement values are distinct according to the determined level of the reliability,
wherein the specific measurement value in which the level of the reliability is determined in the determining process is a representative value which is calculated in the calculating process based on the biological information waveforms that are respectively measured in the measuring process in a plurality of places of a human body, or a waveform based on biological information waveforms of a plurality of beats which are respectively measured in the measuring process in the designated unit time in the plurality of places of the human body, and
wherein the representative value is at least one of: an average value or a median value of the specific measurement values which are calculated respectively in the plurality of places of the human body based on the biological information waveform, or the waveform based on the biological information waveforms of the plurality of beats; and a value which is defined as an interval between an earliest one of start timings and a latest one of end timings of waveform widths defining the specific measurement values appearing in the biological information waveform, or the waveform based on the biological information waveforms of the plurality of beats.

19. A biological information displaying method comprising:
measuring a biological information waveform containing a specific measurement value;
calculating the specific measurement value based on the biological information waveform that is measured in the measuring process in a designated unit time;
determining a level of a reliability of the calculated specific measurement value based on the biological information waveform that is measured in the unit time; and
displaying a trend graph of the specific measurement values while the specific measurement values are distinct according to the determined level of the reliability,
wherein the specific measurement value in which the level of the reliability is determined in the determining process is a representative value which is calculated in the calculating process based on the biological information waveforms that are respectively measured in the measuring process in a plurality of places of a human body, or a waveform based on biological information waveforms of a plurality of beats which are respectively measured in the measuring process in the designated unit time in the plurality of places of the human body, and
wherein, in the displaying process, further displaying the biological information waveform or the waveform based on the biological information waveforms of the plurality of beats, which is used as a basis for calculating the specific measurement value in a designated time, of the specific measurement values displayed in the trend graph of the specific measurement values.

20. The biological information displaying method according to claim 19, wherein, in the displaying process, while corresponding with the biological information waveform or the waveform based on the biological information waveforms of the plurality of beats, which is used as the basis for calculating the specific measurement value in the designated time, of the specific measurement values displayed in the trend graph of the specific measurement values, further displaying level relationships of the specific measurement values which are calculated based on the biological information waveform or the waveform based on the biological information waveforms of the plurality of beats in a form of a graph or numerical values.

21. The biological information displaying method according to claim 20, wherein, in the displaying process, in a case where the level relationships of the specific measurement values are displayed in the form of the numerical values, displaying the specific measurement values in a manner that maximum and minimum values of the numerical values are distinguishable.

22. The biological information displaying method according to claim 20, wherein, in the displaying process, displaying the biological information waveform or the waveform based on the biological information waveforms of the plurality of beats, with superimposed on a display showing starting and ending timings of a time width defining the representative value.

23. A biological information displaying apparatus comprising:
    a measuring circuit which is configured to measure a biological information waveform containing a specific measurement value;
    at least one computer which is configured to calculate the specific measurement value based on the biological information waveform that is measured by the measuring circuit in a designated unit time;
    the at least one computer being further configured to determine a level of a reliability of the calculated specific measurement value, based on the biological information waveform that is measured by the measuring circuit in the unit time; and
    a display which is configured to display a trend graph of the specific measurement values while the specific measurement values are distinct according to the determined level of reliability,
    wherein the at least one computer determines the level of reliability according to a condition which is designated with respect to a degree of fluctuation of the biological information waveform in a designated time zone, and
    wherein the designated time zone for the biological information waveform is an arbitral time zone in which a baseline is appearable in the biological information waveform.

24. The biological information displaying apparatus according to claim 23, wherein a statistical value of the specific measurement values in which the reliability is determined to be high by the at least one computer, in a predetermined time period is displayed superimposedly on the trend graph of the specific measurement values.

25. The biological information displaying apparatus according to claim 24, wherein the display further displays a relationship among: the specific measurement value in a designated time, of the specific measurement values displayed in the trend graph of the specific measurement values; a statistical value of the specific measurement values during a predetermined time period in the designated time; and dispersion of the specific measurement values in the designated time.

26. The biological information displaying apparatus according to claim 25, wherein, in a case where the representative value is designated as a median value of the specific measurement values which are calculated based on the biological information waveforms that are measured in a plurality of places of a human body, or a waveform based on the biological information waveforms of a plurality of beats, the display displays the biological information waveforms or the waveform based on the biological information waveforms of the plurality of beats, and the specific measurement value in a manner that at least one of the biological information waveform which provides the median value, the waveform based on the biological information waveforms of the plurality of beats, and the median value which is calculated based on these waveforms is distinguishable.

27. The biological information displaying apparatus according to claim 23, wherein the specific measurement value is a representative value which is calculated based on the biological information waveforms that are respectively measured by the measuring circuit in a plurality of places of a human body, or a waveform based on biological information waveforms of a plurality of beats which are respectively measured by the measuring circuit in the designated unit time in the plurality of places of the human body.

28. The biological information displaying apparatus according to claim 27, wherein the waveform based on the biological information waveforms of the plurality of beats is a waveform which is obtained by arithmetically averaging the electrocardiogram waveforms of the plurality of beats, or a median value.

29. The biological information displaying apparatus according to claim 27, wherein the representative value is at least one of: an average value or a median value of the specific measurement values which are calculated respectively in the plurality of places of the human body based on the biological information waveform, or the waveform based on the biological information waveforms of the plurality of beats; and a value which is defined as an interval between an earliest one of start timings and a latest one of end timings of waveform widths defining the specific measurement values appearing in the biological information waveform, or the waveform based on the biological information waveforms of the plurality of beats.

30. The biological information displaying apparatus according to claim 27, wherein the display further displays the biological information waveform or the waveform based on the biological information waveforms of the plurality of beats, which is used as a basis for calculating the specific measurement value in a designated time, of the specific measurement values displayed in the trend graph of the specific measurement values.

31. The biological information displaying apparatus according to claim 30, wherein, while corresponding with the biological information waveform or the waveform based on the biological information waveforms of the plurality of beats, which is used as the basis for calculating the specific measurement value in the designated time, of the specific measurement values displayed in the trend graph of the specific measurement values, the display further displays level relationships of the specific measurement values which are calculated based on the biological information waveform or the waveform based on the biological information waveforms of the plurality of beats, in a form of a graph or numerical values.

32. The biological information displaying apparatus according to claim 31, wherein, in a case where the level relationships of the specific measurement values are displayed in the form of the numerical values, the display displays the specific measurement values in a manner that maximum and minimum values of the numerical values are distinguishable.

33. The biological information displaying apparatus according to claim 31, wherein the display displays the biological information waveform or the waveform based on the biological information waveforms of the plurality of beats, with superimposed on a display showing starting and ending timings of a time width defining the representative value.

* * * * *